United States Patent [19]

Engle et al.

[11] 4,403,614
[45] Sep. 13, 1983

[54] IMPLANTABLE CARDIOVERTER

[75] Inventors: William R. Engle, Blaine, Minn.; E. Neil Moore, Jr., Wallingford; Joseph F. Spear, Jr., Philadelphia, both of Pa.; Ronald H. Rockland, Parsippany, N.J.

[73] Assignee: Medtronic, Inc., Minneapolis, Minn.

[21] Appl. No.: 239,007

[22] Filed: Feb. 27, 1981

Related U.S. Application Data

[63] Continuation of Ser. No. 58,847, Jul. 19, 1979, abandoned.

[51] Int. Cl.³ .............................................. A61N 1/36
[52] U.S. Cl. ................................. 128/419 D; 128/705; 128/239; 128/7
[58] Field of Search ........................... 128/419 D, 705

[56] References Cited

U.S. PATENT DOCUMENTS

| | | | |
|---|---|---|---|
| 2,566,876 | 3/1971 | Stoft et al. | 128/419 D |
| 3,857,398 | 12/1974 | Rubin | 128/419 D |
| 4,077,413 | 3/1978 | Partridge | 128/419 D |

Primary Examiner—William E. Kamm
Attorney, Agent, or Firm—Schroeder, Siegfried, Vidas & Arrett

[57] ABSTRACT

A body implantable ventricular cardioverting system. Circuitry is provided which detects the onset of a malignant ventricular tachyarrhythmia and provides a cardioverting signal in response thereto. The cardioverting signal has an energy level that is high relative to the pacing threshhold but below that necessary for defibrillation. In this manner, a ventricular tachyarrhythmia can be cardioverted before the onset of fibrillation and at a lower energy than required for defibrillation. Dependent on such factors as patient threshholds, the tissue/electrode interface and the electrode system employed, the energy level of the cardioverting signal is from 5 millijoules to 15 joules. The system can be configured such that increasingly malignant tachyarrhythmias result in higher energy cardioverting signals, including signals capable of defibrillation. Successful cardioversion with a signal having an energy level lower than necessary for defibrillation reduces the physical damage to the heart as well as the trauma to and discomfort of the patient.

18 Claims, 5 Drawing Figures

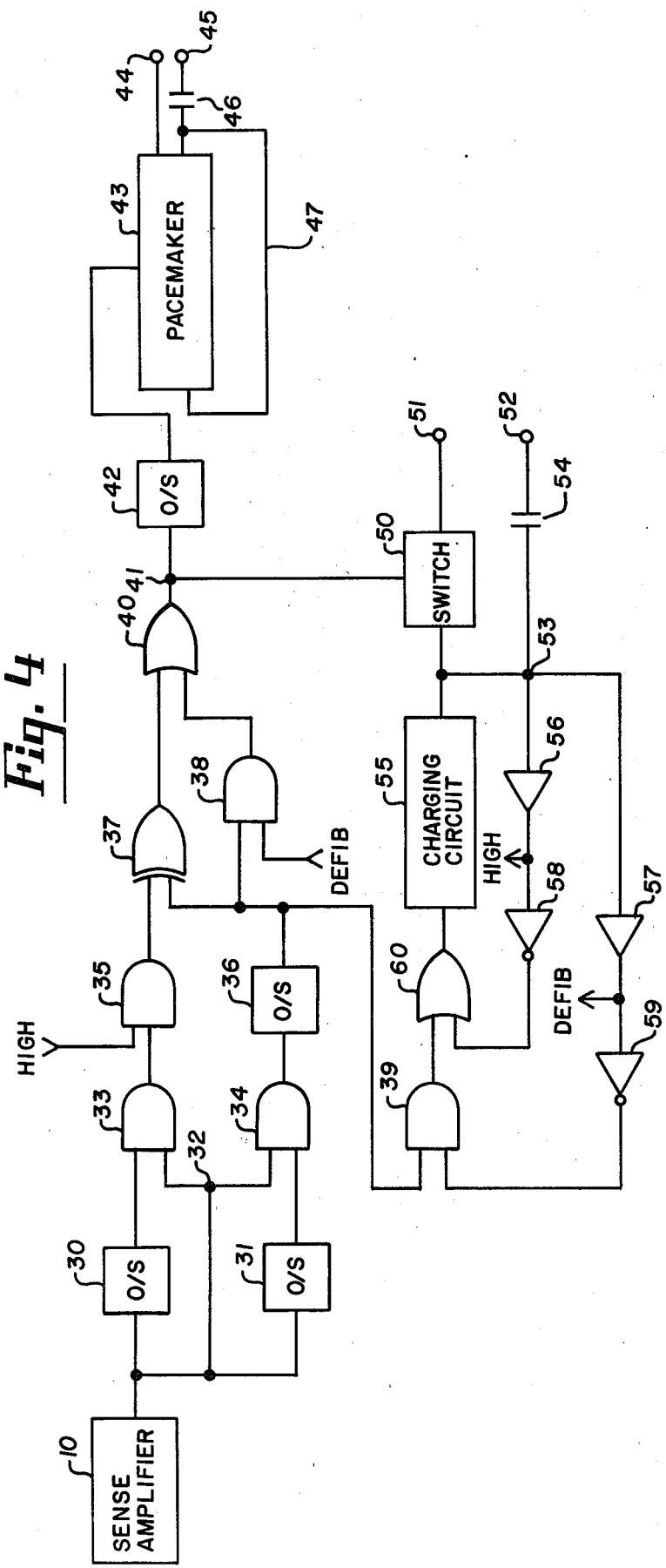
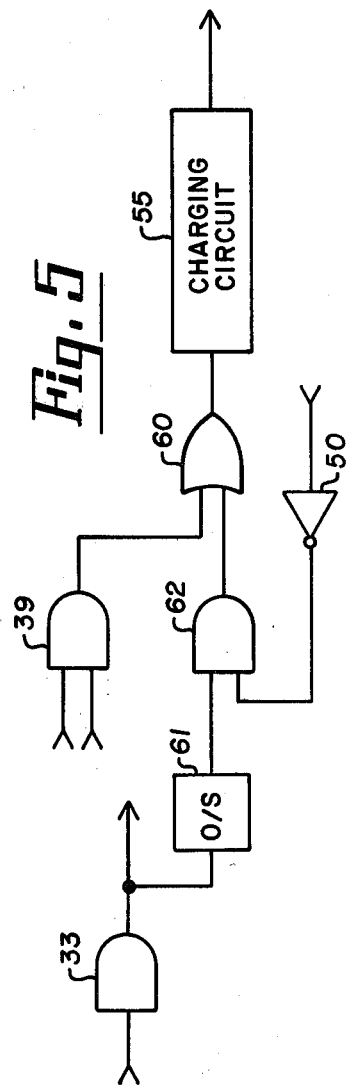
Fig. 4
Fig. 5

IMPLANTABLE CARDIOVERTER

This is a continuation of application Ser. No. 058,847, filed July 19, 1979 now abandoned.

DESCRIPTION

Background of Prior Art

Recent decades have seen much scientific effort directed to the study and treatment of various cardiac arrhythmias, both lethal and non-lethal. Many patients have benefited from these efforts. For example, it is well known that atrial and ventricular tachycardias and fibrillation can be reversed by appropriate electrical stimulation or cardioversion. Unfortunately, the necessary equipment is often available only in a sophisticated medical environment. Thus, those individuals who experience a cardiac arrhythmia that culminates in ventricular fibrillation too often do not have the benefit of this technology. More than one half of the deaths from coronary heart disease occur suddenly, outside the hospital, with the majority being believed to result from a disturbance in cardiac electrical activity which culminates in ventricular fibrillation.

To counter the situation described above, automatic cardiac defibrillators have been proposed. Examples of such devices are disclosed in U.S. Pat. No. 3,614,954 for Electronic Standby Defibrillator in the name of Mirowski et al and U.S. Pat. No. 3,614,955 for Standby Defibrillator and Method of Operation in the name of Mirowski, both issued Oct. 26, 1971. While studies of such systems are encouraging, they nonetheless require high voltages (1,000 volts) and large energies (45 joules). Such large voltage and energy levels produce severe pain which requires that the patient enter a severely hypodynamic state resulting in a loss of consciousness before the therapy is initiated. Also because of the high levels, an improperly applied therapeutic shock may itself result in fibrillation. In addition, a device malfunction delivering a shock to a non-fibrillating heart would, at best, be very uncomfortable and is potentially dangerous.

BRIEF SUMMARY OF THE INVENTION

Within this specification and claims, the term ventricular tachyarrhythmia is intended to embrace not only ventricular tachycardia but also premature ventricular contraction and ventricular fibrillation. The term cardioversion is employed as meaning the conversion of a cardiac tachyarrhythmia to a normal or more physiologically tolerable rhythm and specifically includes defibrillation. Also, it is known that some tachyarrhythmias are self-reversing while others culminate in fibrillation. The former are referred to herein as benign, with the later being referred to herein as malignant.

Many studies have been done to establish criteria to distinguish between malignant and benign tachyarrhythmias. For example, it has been suggested that a R-R interval equal to or less than 430 msec., which corresponds to 140 beats per minute, is malignant while R-R intervals greater than 430 msec are benign. Epstein, *Experimental Acute Myocardial Infarction Characterization and Treatment of the Malignant Premature Ventricular Contraction,* CIRCULATION, Vol. XLVII, p. 446, March 1973. Other studies have developed similar indices for the purpose of predicting when a ventricular tachyarrhthmia is likely to culminate in ventricular fibrillation. It has been suggested that ventricular fibrillation may result from an arrhythmia having a heart rate corresponding to 200-300 beats per minute, the upper limit of this range corresponding to a R-R interval of 200 msec. Dodinet and Godin, *STIMUCOUER MEDICAL,* Issue 22, summer 1978, page 103. From these studies, we believe that an R-R interval greater than 430 msecs. is benign and that the onset of a malignant tachyarrhythmia can be detected as the R-R interval approaches 430 msecs. In addition, we believe that an R-R interval approaching 200 msecs. indicates the onset of fibrillation.

The distinction between the onset of a malignant tachyarrhythmia and the onset of fibrillation has little relevance in the prior art. That is, typical prior art devices respond virtually identically to malignant tachyarrythmias and fibrillation—with a defibrillation energy level stimulating signal. However, our studies indicate that a malignant ventricular tachyarrhythmia may be cardioverted prior to the onset of fibrillation at an energy level significantly below that necessary for defibrillation. That is, dependent on patient threshold, the electrode/tissue interface and the electrode system employed, energy levels from about 5 millijoules to 15 joules are capable of cardioverting a malignant ventricular tachyarrhythmia, subject to the cardioversion being initiated immediately on or shortly after the onset of the tachyarrhythmia and prior to the onset of fibrillation. In comparison, the pacing threshold is typically on the order of 50 microjoules while intracardiac defibrillation typically requires 45 joules of energy. The lower energy requirement of the present invention has less potential for damage to the heart tissue and is likely to prove less painful to the patient. Indeed, in some contexts, the energy level necessary for cardioversion may be at a sufficiently low level to be imperceptible to the patient. In addition, the lower energy requirements allow a more feasible implantable device which may be employed either alone or in combination with a defibrillator and/or cardiac pacemaker.

Our studies were conducted with acute, open-chested, pentobarbital anesthetized mongrel dogs. Fibrillation was induced, and the fibrillation threshold established, by the delivery of a train of constant current pulses to the ventricles through bipolar epicardial electrodes during the T wave of every twelfth heart beat. The current was increased incrementally in each successive pulse train until fibrillation ensued. The intensity of the current necessary to cause fibrillation is the ventricular fibrillation threshold. For a more complete discussion of this technique see Moore and Spear, *Ventricular Fibrillation Threshold,* ARCHIVES OF INTERNATIONAL MEDICINE, Vol. 135, p. 446, March, 1975. The effect of a cardioverting signal having an energy level below that necessary for defibrillation was studied in conjunction with a fibrillation-inducing current pulse train. Defibrillation was accomplished in normal manner. Also, a minimum fifteen minute rest period was allowed between each episode of ventricular fibrillation. Delivery of a cardioverting signal at the onset of fibrillation was found to require significantly less energy than subsequently delivered signals. A typical result with a single dog and a concurrently delivered cardioverting signal and pulse train is as follows:

| Sequence | Ventricular Fibrillation Threshold (mamps) | Energy of Cardioverting Signal (m joules) |
| --- | --- | --- |
| 1. | 20 | 0 |
| 2. | 34 | 500 |
| 3. | 40 | 180 |
| 4. | 19 | 0 |

Throughout our study we found that ventricular fibrillation could be consistently prevented with appropriate cardioverting signals and at lower energy levels than is required for defibrillation. Indeed, such cardioverting signals appear to have a protective effect on the same order of magnitude as pharmacological agents known to be useful for increasing the fibrillation threshold.

In essence, the present invention is directed to a body implantable ventricular cardioverter including circuitry for detecting the onset of a malignant ventricular tachyarrhythmia. Circuitry is responsive to the detecting circuitry for providing a cardioverting signal, the cardioverting signal having an energy level that is high relative to the pacing threshold but below that necessary for defibrillation. As used herein, the phrase "high energy level relative to the pacing threshold" means an energy level at least approximately 100 times greater than the pacing threshhold level.

The cardioverter of the present invention includes an energy storage device which may be either charged to the cardioverting energy level, as needed, or continuously maintained at that level. In a preferred embodiment, the detecting circuitry is responsive to the first malignant ventricular tachyarrhythmic event to result in the delivery of the cardioverting signal. As the malignant ventricular tachyarrhythmia progresses toward fibrillation, that is, as R-R interval decreases, the energy level of the cardioverting signal may be selectively increased. In a preferred embodiment, as the R-R interval approaches that indicative of the onset of fibrillation, (an R-R interval of 200 msec.) the cardioverting signal energy is increased to a level sufficient for defibrillation. In this latter configuration, the cardioverter of the present invention may be said to be in combination with a body implantable defibrillator. Additionally, a pacemaker, preferably of the demand type, may be incorporated within the inventive combination to maximize the benefits of the implantable device to the patient. The cardioverting signal may be delivered to the patient via electrodes carried by an endocardial catheter lead of known design or, alternatively, may be delivered via pericardial leads of known design. In either instance, our studies indicate that each electrode should have a surface area of approximately 500 mm² with electrodes of greater or lesser area being found to be less effective or, at best, to offer no advantages. The electrodes should preferably be constructed of an inert (noble) metal, most preferably platinum, to minimize the electrochemical reactions which are accelerated by electrical potentials. Our experience indicates that epicardial electrodes require less energy than endocardial electrodes for the same effect, the advantage to the endocardial electrode system being that less extensive surgery is required on implantation.

BRIEF DESCRIPTION OF THE DRAWINGS

FIG. 4 illustrates another preferred embodiment of the present invention.

FIG. 5 illustrates modifications to the embodiment of FIG. 4.

DETAILED DESCRIPTION OF THE DRAWINGS

Figure 1:
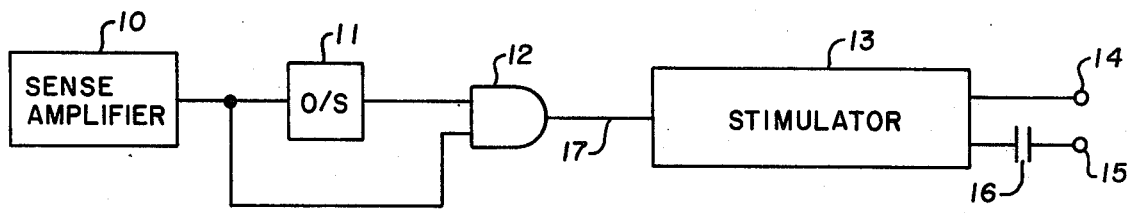
FIG. 1 illustrates the basic aspects of a preferred embodiment of the present invention.

Referring now to FIG. 1 there is illustrated a preferred embodiment of the present invention including a sense amplifier 10 whose output is connected to a one shot 11 and an AND gate 12, the output of the sense amplifier 10 being connected as the second input to AND gate 12. The output of AND gate 12 is connected to a stimulator 13, the stimulator 13 having output electrodes 14 and 15 which are adapted for connection to the heart, in known manner.

Sense amplifier 10 may be of any design known to the prior art capable of detecting R waves and providing an output signal representative of the detection of an R wave. One shot 11 is a negative edge retriggerable device having a period of 430 msecs. Thus, an R wave sensed by sense amplifier 10 will result in the triggering of one shot 11 on the trailing edge of the sense amplifier 10 output causing the output of one shot 11 to go high for 430 msecs. The delay in the response of one shot 11 prevents a single sense amplifier signal from appearing at the input of AND gate 12 during the one shot output it triggered. However, a second R wave sensed by sense amplifier 10 during this 430 msec. interval will result in two high inputs to AND gate 12. As discussed above, an R-R interval of 430 msecs, or less indicates a malignant ventricular tacchyarrhythmia. Thus, a second R wave sensed by sense amplifier 10 during the 430 msec. interval of one shot 11 will result in two high inputs to AND gate 12 and a high output from AND gate 12 representative of a malignant ventricular tachyarrhythmia. If the output of AND gate 12 had been previously low, its going high represents the onset of a malignant ventricular tachyarrhythmia and, specifically, the first malignant ventricular tachyarrhythmic event. Stimulator 13 responds to the high output from AND gate 12 to apply a cardioverting signal across electrodes 14 and 15 noted above, the cardioverting signal has a high energy level relative to the pacemaker threshhold but is below that necessary for defibrillation to reduce the potential damage to the heart tissue and, perhaps, the perception of the signal by the patient.

Figure 2:
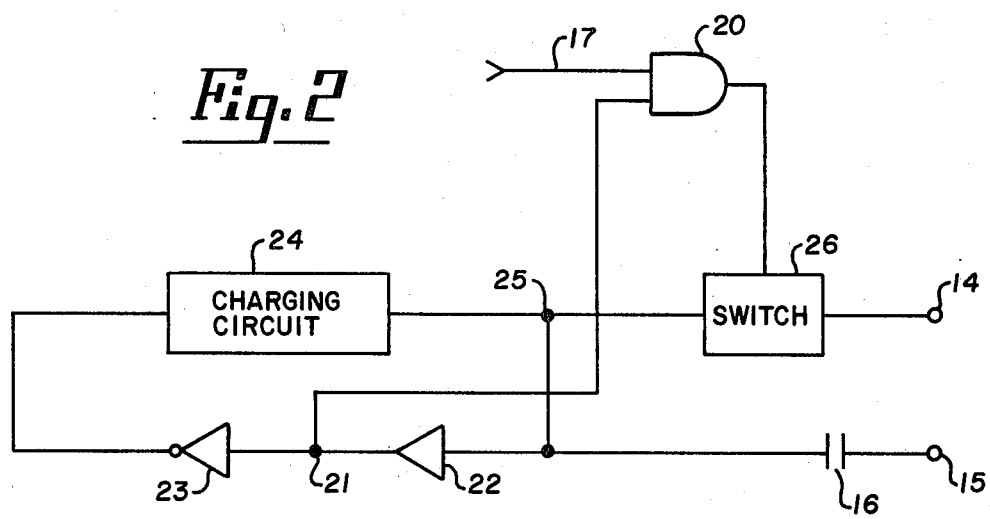
FIG. 2 illustrates a preferred embodiment of a portion of the embodiment illustrated in FIG. 1.

Referring now to FIG. 2, there is shown a preferred embodiment of the stimulator 13 of FIG. 1. A line 17 connects the AND gate 12 to the stimulator 13 and serves as one input to an AND gate 20. The other input to AND gate 20 is connected to a junction 21 which is connected to the output of a comparator 22. Comparator 22 is of a type known to the prior art having an internal reference level against which signals appearing at its input are compared, the output of comparator 22, and thus junction 21, being high if the input to comparator 22 equals or exceeds the reference level and low if the input is below the reference level. Junction 21 is connected to the input of an inverter 23 whose output is connected to a charging circuit 24. The output of charging circuit 24 is connected to a junction 25, the junction 25 being connected to an electronic switch 26, the capacitor 16 and the input of comparator 22. Terminals 14' and 15' are adapted for connection to an appropriate output system such as electrodes 14 and 15 of FIG. 1.

Charging circuit 24 may be a D-C/D-C converter for charging the capacitor 16 to the desired cardioverting energy level. Alternatively, a series of batteries sufficient to supply the required voltage level may be used directly to eliminate the voltage converter. If the batteries have an internal impedance that would prevent the delivery of the stimulation current directly, a filter or storage capacitor may be placed in parallel with the batteries, in known manner. Our studies indicate that a 15 uf capacitor charged to 65 volts works well to deliver the necessary energy levels. Also, switch 26 is preferably a triggerable solid state switch controlled to deliver the energy stored in capacitor 16 when triggered. Preferably, this is accomplished with an SCR arrangement. Also, it is known to the prior art that a truncated capacitor discharge resulting in a trapezoidal signal wave form (as by interrupting the delivery of the energy to the heart before the entire charge has been delivered) is preferable in a cardioverting context. Such an arrangement is disclosed in U.S. Pat. No. 3,805,795, issued Apr. 23, 1974 in the name of Denniston et al, which is co-owned with the present invention and which is hereby incorporated by reference.

In operation, the stimulator embodiment of FIG. 2 maintains a cardioverting level charge on capacitor 16 so as to deliver a high energy level cardioverting signal across the terminals 14' and 15' on the appearance of the first high output signal from AND gate 12 on line 17 (See FIG. 1). Assuming a charge on capacitor 16 below that desired, the output of comparator 22 is low causing the junction 21 to be low and one input of AND gate 20 to be low, thereby effectively preventing the output of AND gate 20 from going high. The low signal at junction 21 is inverted by inverter 23 to result in a high input to charging circuit 24, the high input to charging circuit 24 causing the capacitor 16 to charge under its control, in known manner. When the charge on capacitor 16 reaches the desired level, the output of comparator 22 will go high resulting in a high input to AND gate 20 and a low input to charging circuit 24. The low input to charging circuit 24 causes it to stop charging the capacitor 16, in known manner, while the high input to AND gate 20 allows a high input on line 17 to cause the output of AND gate 20 to go high. When the output of AND gate 20 is high, switch 26 is on connecting the capacitor 16 across the output terminals 14' and 15'. As noted above, switch 26 should be controlled to maintain the on state during the output pulse independently of the output of AND gate 20. An SCR arrangement is suitable for this purpose.

Figure 3:
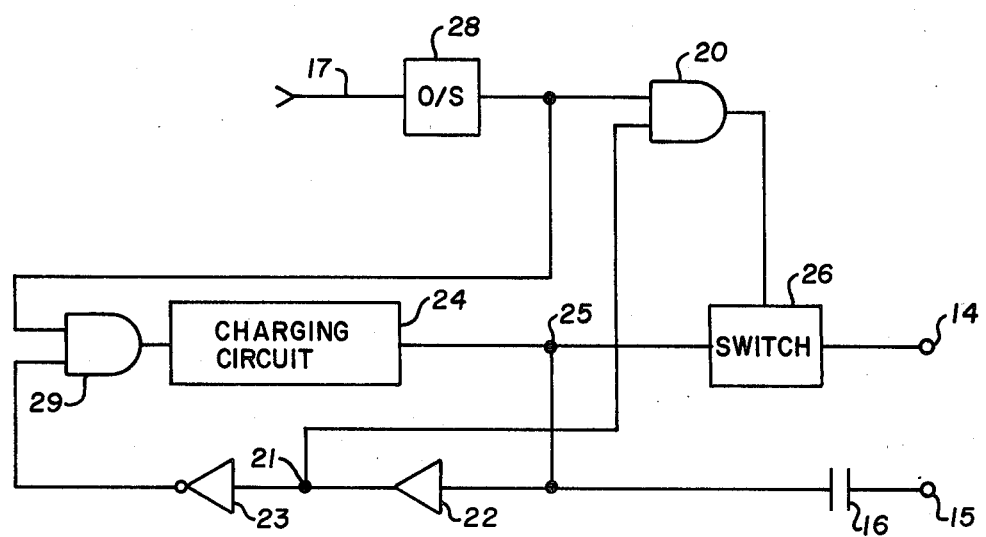
FIG. 3 illustrates an alternative to the embodiment of FIG. 2.

Referring now to FIG. 3 there is shown a modification to the embodiment of FIG. 2 in which the output capacitor 16 is charged to the desired energy level when the delivery of a cardioverting signal is necessary. In FIG. 3, components having the same function as the components illustrated in FIG. 2 are designated by the same reference numeral. FIG. 3 differs from the embodiment of FIG. 2 by the addition of a one shot 28 connected to the output of AND gate 12 (See FIG. 1), one shot 28 providing an input to AND gate 20, and by the addition of an AND gate 29 having one input connected to the output of one shot 28 and the other input connected to the output of inverter 23. The output of AND gate 29 is connected to the charging circuit 24. As mentioned above, in the embodiment of FIG. 3, capacitor 16 is not maintained at the desired cardioverting energy level. Instead, capacitor 16 is charged to that level when a malignant ventricular tachyarrhythmia is detected as indicated by the output of AND gate 12 (See FIG. 1) and, accordingly, the input to one shot 28 going high. One shot 28 is a retriggerable device having a period the same as that of one shot 11 (See FIG. 1) such that one shot 28 is triggered at the onset of a malignant ventricular tachyarrhythmia and remains triggered for the duration of the tachyarrhythmia.

In operation, a high signal appearing on line 17 triggers one shot 28 causing one input of AND gates 20 and 29 to go high. However, the charge on capacitor 16 is below the reference level of comparator 22 causing a low signal to appear at junction 21 and at the other input of AND gate 20. Thus, switch 26 remains open. The low at junction 21 is inverted by inverter 22 to appear as a second high input to AND gate 29 providing a high output and causing the charger circuit 24 to charge the capacitor 16. When the charge on capacitor 16 reaches the reference level of comparator 22, the output of comparator 22 goes high providing a second high input to AND gate 20 and resulting in a high output from AND gate 20 to trigger or close switch 26 to apply the charge on capacitor 16 across the terminals 14' and 15'. As in the embodiment of FIG. 2, the switch 26 maintains the closed state for the duration of the cardioverting signal and may be controlled so as to interrupt the delivery of the cardioverting energy to the heart before the entire charge has been delivered to thus generate a truncated capacitor discharge, as described above.

Referring now to FIG. 4 there is illustrated a preferred embodiment of the present invention in combination with a pacemaker. In the embodiment of FIG. 4, the energy level of the cardioverting signals increases as the malignant tachyarrhythmia progresses toward or to fibrillation. That is, as the R-R interval decreases, the energy level of the cardioverting signal is increased. The increased energy level may be sufficient for defibrillation and the progression of the tachyarrhythmia can be a progression to fibrillation within the context of the illustrated embodiment. Indeed, in the discussion of FIG. 4, the increased energy cardioverting signal will be described as a defibrillating signal.

In FIG. 4, there is illustrated a sense amplifier 10 of the type described with reference to FIG. 1. The output of the sense amplifier 10 is connected to the input of one shots 30 and 31 and to a junction 32. An AND gate 33 has its inputs connected to the output of one shot 30 and the junction 32. Similarly, an AND gate 34 has its inputs connected to the junction 32 and the output of one shot 31. One shots 30 and 31 are retriggerable devices that are triggered on the negative or trailing edge of the signals from sense amplifier 10 to provide a delay such that a signal appearing at junction 32 that triggered one shots 30 and 31 does not result in two high inputs to AND gates 33 and 34.

The output of AND gate 33 is connected as one input to an AND gate 35, the other input of AND gate 35 being connected to receive a HIGH signal to be described more fully below. The output of AND gate 34 is connected to trigger a one shot 36, one shot 36 being triggered on the leading edge of the output from AND gate 34. The output of one shot 36 and AND gate 36 are connected as inputs to an exclusive OR gate 37, with one shot 36 also being connected to one input of AND gate 38 and to one input of AND gate 39. The other input of AND gate 38 is connected to receive a DEFIB signal to be described more fully below. The outputs of exclusive OR gate 37 and AND gate 38 are connected to the inputs of an OR gate 40 whose output is connected to a junction 41. Junction 41 is connected to a one shot 42, the output of one shot 42 being connected to inhibit a pacemaker 43 during the time that its output is high. Preferably, pacemaker 43 is a demand type unit having output electrodes 44 and 45, an output capacitor 46 and its own sense amplifier connected to the output of the pacemaker via line 47. Junction 41 is also connected to toggle an electronic switch 50 on the appearance of a high signal at the junction 41.

The cardioverting signals generated by the embodiment of FIG. 4 are applied across terminals 51 and 52. Terminal 52 is connected to a junction 53 by a capacitor 54. Junction 53 is connected to a charging circuit 55 and to comparators 56 and 57. The output of comparator 56 provides the HIGH signal and is connected to an inverter 58 while the comparator 57 provides the DEFIB signal and is connected to an inverter 59. Inverter 59 provides the other input to AND gate 39, the output of AND gate 39 providing one input to OR gate 60. Inverter 58 provides the other input to OR gate 60, the output of OR gate 60 being connected to the charging circuit 55.

The embodiment of FIG. 4 maintains capacitor 54 at the first desired cardioverting energy level and increases the charge on the capacitor 54 on progression of the tachyarrhythmia beyond a predetermined condition. For example, one shot 30 may have an output pulse duration of 430 msecs. which corresponds to approximately 140 beats per minute and the onset of a malignant ventricular tachyarrhythmia. One shot 31, on the other hand, can be employed to detect an even shorter R-R interval corresponding to a progression of the tachyarrhythmia. For example, one shot 31 can have an output pulse duration of 200 msecs. corresponding to 300 beats per minute and the onset of fibrillation. One shot 36 has an output pulse duration corresponding to that of one shot 31 although one shot 36 is not negative edge triggered. One shot 42 may have an output pulse duration from 1 to 5 seconds to inhibit the pacemaker for that period of time following delivery of a cardioverting signal to allow its sense amplifier to return to its normal sensing characteristics following the cardioverting signal. With the output pulse durations of one shots 30 and 31 as described above, comparator 56 should have a reference voltage level of approximately 50 volts while comparator 57 should have a reference voltage of approximately 1400 volts. It is known that a truncated defibrillation shock can be effective at lower voltages. Accordingly, if switch 50 were controlled to provide such a truncated signal, the reference voltage level for comparator 57 may be established at approximately 1,000 volts.

In operation, and assuming no existing malignant ventricular tachyarrhythmia, sense amplifier 10 provides an output on each sensed R wave. The fact that one shots 30 and 31 are negative edge triggered allows the sense amplifier output signal to disappear from junction 32 prior to the firing of the one shots 30 and 31. Thus, one shots 30 and 31 are triggered on each sensed R wave but the output of AND gates 33 and 34 remains low in the absence of a subsequent sensed R wave during the output pulses of one shots 30 and 31, respectively. Assuming the onset of a malignant tachyarrhythmia, an R-R interval equal to or less than 430 msecs., but greater than 200 msecs., the first sensed R wave will trigger one shots 30 and 31 while the next sensed R wave (the first tachyarrhythmic event) comes within the output pulse of one shot 30 but outside the output pulse of one shot 31. Accordingly, the output of AND gate 33 will go high while the output of AND gate 34 will remain low. Inasmuch as capacitor 54 is charged to the reference level of comparator 56, the output of comparator 56 will be high resulting in two high inputs to AND gate 35 and a single high input to exclusive OR gate 37. Accordingly, junction 41 will go high causing switch 50 to apply the charge on capacitor 54 across the terminals 51 and 52. For so long as the tachyarrhythmia continues, capacitor 54 will be repetitively charged to the reference level of comparator 56 to be repetitively connected across the terminals 51 and 52. However, should the tachyarrhythmia progress such that the R-R interval equals 200 msecs. or less, the output of both AND gates 33 and 34 will go high. This will result in a triggering of one shot 36 resulting in the charging circuit 55 charging the capacitor 54 to the reference level of comparator 57. When the charge on capacitor 54 reaches the reference level of converter 57, the DEFIB signal goes high resulting in a high output from AND gate 38 and a toggling of switch 50 to apply the charge on capacitor 54 across the terminals 51 and 52. This increased energy cardioverting signal will be repetitively applied through repetitive charges of capacitor 54 until the tachyarrhythmia is cardioverted.

FIG. 5 illustrates a modification to the embodiment of FIG. 4 in which like reference numerals designate like elements. The embodiment of FIG. 5 includes all of the elements of FIG. 4, only those elements associated with the modification being illustrated for the sake of brevity. In FIG. 5, one shot 61 and AND gate 62 have been added to the circuitry illustrated in FIG. 4 to provide for a charging of capacitor 54 to the reference level of comparator 56 on the onset of the malignant tachyarrhythmia. This modification is essentially that illustrated in FIG. 3 as a modification of the embodiment of FIG. 2. Except as illustrated in FIG. 5, the other circuit elements forming the embodiment of FIG. 5, are connected as illustrated in FIG. 4.

Obviously, many modifications and variations of the present invention are possible in light of the above teachings. For example, as noted above, the present invention may be employed alone as a cardioverter or in combination with a defibrillator and/or pacemaker. Additionally, an embodiment of the present invention may be configured in accordance with the above teachings to provide multiple increases in the energy level of the cardioverting signal on increasing progression of the malignant tachyarrhythmia from its onset to fibrillation. Other parameters may be employed to establish the onset of a malignant ventricular tachyarrhythmia and its progression. Cardioversion energy levels other than those disclosed may also be employed. However, with the parameters disclosed herein, malignant ventricular tachyarrhythmia may be cardioverted before it progresses to fibrillation and at energy levels below that necessary for defibrillation. It is therefore to be understood that, within the scope of the appended claims, the invention may be practiced otherwise than as specifically described.

We claim:

1. A body implantable ventricular cardioverter which comprises:

means for detecting the onset of a malignant ventricular tachyarrhythmia;

means responsive to the detecting means for providing a cardioverting signal, said cardioverting signal having an energy level that is high relative to a typical pacing threshold of 50 microjoules and below 45 joules that is typically necessary for defibrillation.

2. The cardioverter of claim 1 wherein said detecting means comprises means responsive to the first malignant ventricular tachyarrhythmic event.

3. The cardioverter of claim 1 wherein said cardioverting signal providing means comprises means for storing the energy for said cardioverting signal.

4. The cardioverter of claim 3 wherein said cardioverting signal providing means comprises means for charging said energy storing means in response to the onset of a malignant ventricular tachyarrhythmia.

5. The cardioverter of claim 4 wherein said detecting means comprises means responsive to the first malignant ventricular tachyarrhythmic event.

6. The cardioverter of claim 3 wherein said cardioverting signal providing means comprises means for maintaining said energy storing means in a charged state.

7. The cardioverter of claim 6 wherein said detecting means comprises means responsive to the first malignant ventricular tachyarrhythmic event.

8. The cardioverter of claim 1 wherein said cardioverting signal providing means repetitively provides cardioverting signals during said tachyarrhythmia.

9. A body implantable cardioverter which comprises:

means for detecting the onset of a malignant ventricular tachyarrhythmia;

means responsive to the detecting means for providing a cardioverting signal having an energy level from 5 millijoules to 15 joules; and output means for delivering said cardioverting signal.

10. The cardioverter of claim 9 wherein said output means comprises endocardial electrode means, the energy level of said cardioverting signal being from 10 joules to 15 joules.

11. The cardioverter of claim 10 wherein said endocardial electrode means each have a surface area of approximately 500 mm².

12. The cardioverter of claim 9 wherein said output means comprises epicardial electrode means, the energy level of said cardioverting signal being from 5 millijoules to 250 millijoules.

13. The cardioverter of claim 12 wherein said epicardial electrode means comprise circular means each having a contact surface area of approximately 500 mm².

14. The cardioverter of claim 9 wherein said detecting means comprises means responsive to the first malignant ventricular tachyarryhmic event.

15. The cardioverter of claim 9 wherein said cardioverting signal providing means repetitively provides cardioverting signals during said tachyarrhythmia.

16. The method of cardioverting malignant ventricular tachyarrhythmias which comprises:

detecting the onset of a malignant ventricular tachyarrhythmia; and delivering, in response thereto, a cardioverting signal having an energy level that is high relative to a typical pacing threshold of 50 microjoules and below 45 joules that is typically necessary for defibrillation.

17. The method of claim 16 wherein the step of delivery comprises the step of delivering a cardioverting signal having an energy level from 5 millijoules to 15 joules.

18. The method of claim 17 wherein the step of delivering comprises the step of repetitively delivering said cardioverting signals during said tachyarrhythmia.

* * * * *

UNITED STATES PATENT AND TRADEMARK OFFICE
CERTIFICATE OF CORRECTION

PATENT NO. : 4,403,614

DATED : September 13, 1983

INVENTOR(S) : William R. Engle et al

It is certified that error appears in the above-identified patent and that said Letters Patent are hereby corrected as shown below:

The title of the invention appearing in the patent as "IMPLANTABLE CARDIOVERTER" should read --IMPLANTABLE CARDIOVERTING SYSTEM--.

Column 4, line 40, the word appearing as "tacchyarrhythmia" should read --tachyarrhythmia--.

Column 6, line 68, after the word "gate" (second occurrence) the numeral appearing as "36" should read --35--.

Signed and Sealed this

Twentieth Day of December 1983

[SEAL]

Attest:

GERALD J. MOSSINGHOFF

Attesting Officer     Commissioner of Patents and Trademarks